United States Patent [19]

Brazdil et al.

[11] Patent Number: 4,873,215
[45] Date of Patent: * Oct. 10, 1989

[54] CATALYST FOR AMMOXIDATION OF PARAFFINS

[75] Inventors: James F. Brazdil, Mayfield Village; Andrew T. Guttmann, Maple Heights, both of Ohio

[73] Assignee: The Standard Oil Company, Cleveland, Ohio

[*] Notice: The portion of the term of this patent subsequent to Oct. 3, 2006 has been disclaimed.

[21] Appl. No.: 49,252

[22] Filed: May 13, 1987

Related U.S. Application Data

[62] Division of Ser. No. 919,105, Oct. 15, 1986, abandoned.

[51] Int. Cl.$^4$ .................... B01J 27/182; B01J 27/185; B01J 27/188; B01J 27/198
[52] U.S. Cl. ...................................... 502/202; 502/209
[58] Field of Search ................................ 502/202, 209

[56] References Cited

U.S. PATENT DOCUMENTS

| | | | |
|---|---|---|---|
| 3,591,620 | 7/1971 | Yoshino et al. | 502/209 X |
| 3,686,267 | 8/1972 | Taylor | 558/319 |
| 3,860,534 | 1/1975 | Harris et al. | 502/353 |
| 3,988,359 | 10/1976 | Saito et al. | 502/202 X |
| 4,436,671 | 3/1984 | Furuoya et al. | 558/319 |

FOREIGN PATENT DOCUMENTS 1336136  11/1973  United Kingdom ................ 558/319

*Primary Examiner*—W. J. Shine
*Attorney, Agent, or Firm*—C. S. Lynch; D. J. Untener; L. W. Evans

[57] ABSTRACT

Disclosed is a process for the ammoxidation of paraffins having 3-5 C atoms using a complex metal oxide catalyst having the ingredients and the proportions which are represented by the following empirical formula:

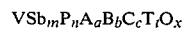

$$VSb_mP_nA_aB_bC_cT_tO_x$$

where
A is one or more of W, Wn, Mo, B and Ge;
B is one or more of Fe, Co, Ni, Cr, Mn, Cu, Zn, Se, Te, Pb and As;
C is one or more of an alkali metal and Tl
T is one or more of Ca, Sr and Ba and where m is greater than 1 and up to 10; n is greater than zero and up to 10, a is 0-10; b is 0-3; c is 0-1; t is 0-1; a is equal to or less than m; b is equal to or less than m; n is equal to or less than m; and wherein the antimony has an average valency higher than +3 and the vanadium has an average valency lower than +5, and the catalyst and how to make the catalyst.

14 Claims, No Drawings

CATALYST FOR AMMOXIDATION OF PARAFFINS

This application is a division of co-pending application Ser. No. 919,105 filed Oct. 15, 1986, now abandoned.

This invention relates to a catalytic ammoxidation of paraffins containing from 3 to 5 carbon atoms to $\alpha,\beta$-unsaturated nitriles, especially paraffins containing 3 to 4 carbon atoms, Most important is the ammoxidation of propane to acrylonitrile.

Because of the price differential between propylene and propane an economic incentive exists for the development of a viable catalytic process for conversion of propane to acrylonitrile.

Early attempts to develop an efficient process for the ammoxidation of propane to acrylonitrile produced either insufficient yields or processes that necessitated adding halogen promoters to the feed. The latter procedure would require not only reactors made of special corrosion resistant materials, but also the quantitative recovery of the promoter. The added costs thus eliminated the advantage of the propane/propylene price differential.

It is thus an object of the present invention to provide an improved process for the ammoxidation of paraffins to unsaturated nitriles.

It is a further object of the invention to provide new catalysts for such reaction.

Still another object is to provide an improved catalytic ammoxidation process for making unsaturated nitriles from lower paraffins without the use of halogen promoters.

Other objects as well as aspects, features and advantages, of the present invention will become apparent from a study of the accompanying disclosure and the claims.

These and other objects are achieved by the present invention according to one aspect of which there is provided a process for making a $C_3$ to $C_5$ nitrile by the ammoxidation of paraffins containing 3 to 5 carbon atoms by the catalytic reaction of such paraffins with oxygen and ammonia by catalytic contact with a complex metal oxide catalyst having the ingredients and the proportions which are represented by the following empirical formula:

$$VSb_mP_nA_aD_bC_cT_tO_x \qquad \text{formula (1)}$$

where

A is one or more of W, Sn, Mo, B and Ge;
D is one or more of Fe, Co, Ni, Cr, Mn, Cu, Zn, Se, Te, Pb and As;
C is one or more of an alkali metal and Tl
T is one or more of Ca, Sr and Ba
and where m is greater than 1 and up to 10 (usually 2-10, most usually 3-7); n is greater than zero and up to 10 (usually 0.1-5, most usually 0.1-1); a is 0-10; b is 0-3; c is 0-1; t is 0-1; a is equal to or less than m; b is equal to or less than m; n is equal to or less than m; and wherein the antimony has an average valency higher than $+3$ and the vanadium has an average valency lower than $+5$.

The foregoing catalyst is usually on an inorganic oxide support material. All of the subscripts in formula (1) are of course atoms. A now preferred support material is alumina or silica-alumina, as further discussed herein.

It should be noted that the present ammoxidation reaction is effected in the substantial absence of halogen or sulfur or compounds thereof. Preferably also, a halide or halogen is not employed in any stage in the preparation of the catalyst.

The present process is especially useful in the ammoxidation of propane and isobutane.

Particularly useful catalyst compositions of the foregoing description are those in which a is at least 0.2 and includes at least 0.2 atoms of W.

According to the present invention the foregoing catalysts are prepared under conditions such that in the final composition the average oxidation state of vanadium is less than 5. One method for preparing the catalysts of the present invention involves a redox reaction between a compound of trivalent antimony such as $Sb_2O_3$ and a compound of pentavalent vanadium such as $V_2O_5$, during which at least part of the antimony is oxidized and at least part of the vanadium is reduced.

The foregoing redox reaction was described by Birchall and Sleight (*Inorganic Chem.* 15, 868–70 [1976]) and by Berry et al. (*J. Chem. Soc. Dalton Trans.*, 1983, 9–12), who effected the reaction by heating a dry mixture of the above reactants at temperatures above 600° C. Berry characterized the product as $VSb_{1-y}O_{4-1.5y}$ where $0<y<0.1$. This product has a tetragonal rutile-type crystalline structure with a unique x-ray diffraction pattern.

The redox reaction can successfully and more conveniently be carried out in an aqueous medium, at a lower temperature by heating at a temperature of at least 80° C. and up to 200° C., for instance, by heating an aqueous dispersion of a $V^{+5}$ compound, such as $NH_4VO_3$ or  $2O_5$, with an $SB^{3+}$ compound where the $Sb^{3+}$ compound is in excess as noted above, usually in admixture with an inorganix oxide support material, where m is $>1$ and up to 20 and wherein any unreacted antimony is in the form of antimony trioxiide, the V has an average valence less than $+5$ and the reacted Sb has an average valence more than $+3$, and wherein the atoms of Sb over $m=1$ are present at least in part as $Sb_2O_3$ and the support material usually used is present from 10 to 90 weight percent, usually from 20–75 weight percent, of the total slurry solids on a dry oxide basis.

Usually, in the above precursor slurries m is 2–10, more usually 3–7.

The catalyst precursor slurry can be dried and calcined in a molecular oxygen containing gas at temperatures of 350° to 850° C., usually 400° to 650° C., to produce a catalyst useful in the process of the invention for ammoxidizing $C_3$ to $C_5$ paraffins. The additive, P, A, B, C and/or T can be added in the slurry after the redox reaction, or the solid particles containing the vanadium and antimony values after separation from the aqueous medium can be coated or impregnated in a known manner with such additives at any suitable stage prior to final calcination of the catalyst.

If the phosphorus promoted vanadium-antimony catalysts are prepared by using pentavlent vanadium and pentavalent antimony compounds, thus eliminating the redox reacton, both the vanadium and antimony remain in the high oxidation state and the resulting catalyst is very inferior, with or without additives. Also, inferior catalysts result when the vanadium-antimony precursor is made by reacting $Sb_2O_3$ and $V_2O_5$ (or other $V^{5+}$ compound) in the presence of compounds that act as oxidizing or reducing agents, such as nitric acid, nitrates, or multivalent ions, since these tend to interfere with the desired redox reaction between anitomony and vanadium.

Thus, according to the present invention the superior catalytic performance in paraffin ammoxidation is obtained with the catalysts of the invention which contain a complex vanadium-antimony oxide composition containing phosphorus, with vanadium in a low oxidation state less than +5 and antimony in a high oxidation state greater than +3, usually plus an inorganic oxide support.

In the usual practice of the present invention the catalyst support/diluent for the catalyst of formula (1) is not an oxide of an element named in formula (1). Now preferred support materials are silica-alumina and alumina as previously noted herein.

In formula (1) subscript a usually is at least 0.2, more usually at least 0.4 or 0.5. In formula (1) at least 0.2 atoms of W are usually present per atom of V. A often includes at least 0.4 atoms of W per atom of V.

Phosphorus and the optional elements shown in formula (1) can be incorporated in the base vanadium-/anitomony/support precursor slurry or added to the solids recoverd from the slurry by methods generally known in the art, using oxides, hydroxides, acids, salts (particularly organic salts such as acetates), and other compounds of such elements. Examples of such incorporation are shown in the specific examples hereinafter.

Tungsten is advantageously incorporated as ammonium meta- or orthotungstate, tungstic acid, or tungsten trioxide. P can be introduced, for instance, as ammonium phosphate or $(NH_4)_2HPO_4$ or phosphoric acid.

The catalyst support not only improves mechanical stability of the catalysts, but the catalytic activity is significantly improved, especially in the case of alumina and silica-alumina. Besides alumina and silica-alumina other supports that can be used are silica, titania, silica-titania, $Nb_2O_5$, silica-niobia, silica-zirconia, zirconia, and magnesia, etc.

Now preferred support or diluent materials for not only improving mechanical stability but also for improving the yield of the desired nitriles are selected from silica-alumina and alumina having 20-100, usually 50-100, preferably 60-100 weight percent alumina; silica-titania and titania having 20-100 weight percent titania; silica-zirconia and zirconia having 80-100 weight percent zirconia; and silica-niobia and niobia having 30-100 weight percent niodia ($Nb_2O_5$).

The catalysts of formula (1) can, of course, contain oxides of other elements not set forth in formula (1), as long as they do not materially detrimentally affect the catalytic ammoxidation of the paraffin to the desired nitriles. When bismuth is optionally present in oxidized form as part of the catalyst of formula (1), it is usually present in amounts of no more than 0.2 atoms of Bi per atom of V.

The weight ratio of the catalyst having the ingredients of empirical formulas (1) or (3) to the support material can vary from 9:1 to 1:9.

In the ammoxidation of the present invention, the reaction is preferably carried out in the gas phase by contacting a mixture of the paraffin, ammonia and a molecular oxygen containing gas, such as air, with a catalyst of the inventon contained in a fixed bed, a gravity flowing bed, a fluidized bed or a fast transport reactor mode. It also possible to include additional diluents such as steam, nitrogen, carbon dioxide or helium.

The mole ratio of the paraffin, such as propane to molecular oxygen, can vary from 0.1:1 to 10:1, and a ratio in the range from 0.2:1 to 5:1 is usual. The mole ratio of paraffin (such as propane) to ammonia can vary from 0.2:1 to 16:1, but is usually from 0.4:1 to 5:1.

It should be noted that when operating at ratios of paraffin to oxygen and to ammonia in excess of stoichiometric, 100 percent conversion of paraffin is not even theoretically attainable. However, when so operating, an advantage is that the selectivity of the paraffin to the corresponding nitrile and the corresponding olefin is greatly increased and the olefin can be further ammoxidized with $O_2$ and $NH_3$ to make further quantities of the nitrile. Thus, the nitrile and the corresponding olefin are both useful products of the present process. The unreacted olefin and paraffin can, of course, be fed to an ammoxidation step.

The reaction temperature can vary from 400° to 650° C., but is usually 460° to 520° C. The latter temperature ranges are especially useful in the case of propane ammoxidation to acrylonitrile.

The average contact time is usually from 0.02 to 20 seconds, and is usually from 2 to 8 seconds, but higher or lower contact times can be used.

The catalysts of the present invention are believed to be unique. U.S. Pat. No. 3,860,534, 1975, described catalysts that contain both vanadium and antimony but these are both in a high oxidation state and are thus entirely different from the catalysts of the present invention.

The following examples of the invention are exemplary and should not be taken as in any way limiting.

In the examples the conversion, yield and selectivity are defined as follows:

$$\text{conversion} = \frac{\text{moles paraffin reacted}}{\text{moles paraffin charged}} \times 100\ (\%)$$

$$\text{yield} = \frac{\text{moles product produced}}{\text{moles paraffin charged}} \times 100\ (\%)$$

$$\text{selectivity} = \frac{\text{moles product produced}}{\text{moles paraffin reacted}} \times 100\ (\%)$$

The term per pass conversion when used herein has the same definition as yield.

EXAMPLE 1

A catalyst having the composition 50 wt % $VSb_5WO_x + 50$ wt % $Al_2O_3$ was prepared as follows: An alumina gel was prepared by adding 58.8 g hydrated alumina, 85 wt % $Al_2O_3$ to a mixture of 206 ml distilled water and 29 g of acetic acid. A stable dispersion was obtained which after 3 to 4 hours stirring formed a soft non-flowing gel.

In a separate step 5.40 g of ammonium vanadate, dissolved in 150 ml of distilled water, was refluxed along with 33.6 g of $Sb_2O_3$ for about 16 hours. Following reflux 12.45 g of ammonium metatungstate was added to the hot slurry and the mixture was allowed to partly evaporate with constant stirring. It was then throughly mixed with the alumina gel. The resulting mixture was dried in an evaporating dish for about 16 hours at about 120° C.

The dried material was heat treated in air at 350° C. for 5 hours and then ground and screened and the 20 to 35 mesh particle size was collected. The screened material was finally heat treated at 610° C. in air for 3 hours.

EXAMPLE 2

A catalyst having the empirical formula 50 wt % $VSb_{3.5}P_{0.5}WO_x$+50 wt % $Al_2O_3$ support was made as follows:

In a stirred flask equipped for heating under reflux, 3.81 g $NH_4VO_3$ were dissovled in 90 ml hot water. To the hot solution 16.6 g $Sb_2O_3$ were added, and the slurry was boiled under reflux for 16-18 hours overnight. There was ammonia evolution, and the vanadium antimonate mixture turned gray-green.

In a separate operation, 35.3 g hydrated alumina, 85 wt % $Al_2O_3$ were mixed with 127.2ml $H_2O$ (cold)+14.1g acetic acid (10 percent solution) and stirred until the suspension gelled. It took about 3 hours, and the gel was soft, homogeneous, with the consistency of thick cream.

Meanwhile the vanadium antimonate slurry was transferrred to a beaker. A solution of 8.80 g ammonium meta-tungstate in about 20 ml H2O and a solution of 2.15 g $(NH_4)_2HPO_4$ in $H_2O$ were then added, followed by the addition, with stirring (magnet) of the alumina gel. After partial evaporation, the mixture became too thick for stirring. It was then transferrd to an evaporating dish, and the evaporation, following by drying overnight, was continued in an oven at 110°-120° C. The dried material was precalcined at 350° C. for 5 hours, screened to 20/35 mesh, then calcined 3 hours at 610° C.

EXAMPLE 3

A catalyst having the composition 50 wt % $VSb_5PWO_x$+50 wt % $Al_2O_3$ was prepared as follows: 15.0 g of ammonium vanadate was dissolved in about 300 ml of hot distilled water. To this stirred solution was added 10.6 g of 99% $H_3PO_4$ in 25 ml of distilled water. The mixture was refluxed for about 16 hours then evaporated under nitrogen at 85°-90° C. for several hours and then dried at about 135° C. 5.36 g of this dried material was mixed along with 21.90 g of $Sb_2O_3$ and 8.10 g of ammonium metatungstate in 20 ml of distilled water. The resulting slurry was evaporated in an oven at about 120°-125° C. with frequency stirring and then dried in an oven for 6 hours. The dried material was mixed with 40.30 g of hydrated alumina, 85 wt % $Al_2O_3$ and compounded to a paste with 42 ml of distilled water and 5 ml of acetic acid. The mixture was dried at 120° C. in air.

The dried material was heat treated in air at 350° C. or 5 hours and then ground and screened and the 20 to 35 mesh particle size was collected. The screened material was finally heat treated at 610° C. in air for 3 hours.

EXAMPLE 4

A catalyst having the composition 50 wt % $VSb_{3.5}WO_x$+50 wt % $Al_2O_3$ was prepared as follows: An alumina gel was prepared by adding 34.71 g hydrated alumina, 85 wt % $Al_2O_3$ to 125 cc of water, followed by the addition of 13.9 g of glacial acetic acid with stirring; after about 4 hours a gel formed.

In a separate operation 4.14 g of $NH_4VO_3$ was dissolved in 150 cc of hot water with stirring. 18.07 g of $Sb_2O_3$ was added and the mixture was refluxed with stirring overnight. 9.66 g of ammonium metatungstate dissolved in 40 cc of water was added to the refluxing mixture. This mixture was stirring for 15 minutes, placed in a 600 cc beaker, and the alumina gel was added while stirring. The mixture was concentrated by heating at 120° C. in an evaporating dish. It was then heat treated fo 5 hours at 350° C. and then ground and screened. The 20 to 35 mesh particle size material was collected and calcined in air at 610° C. for 3 hours.

EXAMPLE 5

A catalyst having the composition 50 wt % $VSb_5WP_{0.5}O_x$+50 wt % $Al_2O_3$ was prepared as follows: 19.54 g of $Sb_2O_3$ was added to a heated solution of 3.14 g of ammonium vanadate in 90 ml of distilled water and the mixture was refluxed for about 16 hours. The mixture was then transfered to a beaker and heated with stirring. Aqueous solutions of 7.24 g of ammonium metatungstate and 1.77 g of ammonium hydrogen phosphate were then added and the mixture was allowed to partly evaporate with constant stirring. To this was added a dispersion of hydraed alumina, 85 wt % $Al_2O_3$ prepared by mixing 35.3 g of hydrated alumina, 85 wt % $Al_2O_3$ with 1.5 g acetic acid in 140 g of distilled water. The resulting mixture was first evaporated in a beaker with constant sitrring then in an evaporating dish for about 16 hours at about 120° C.

The dried material was heat treated in air at 350° C. for 5 hours and then ground and screened and the 20 to 35 mesh particle size was collected. The screened material was finally heat treated at 610° C. in air for 3 hours.

In the ammoxidation runs of the following examples, the catalyst is in a tubular 3/8 inch I.D. stainless steel fixed bed reactor. The reactor is equipped with a preheat leg immersed in a temperature controlled molten salt bath. The feed is fed over the catalyst for the number of hours noted before the runs are started; the runs of each example last 30 minutes. In all runs the weight of propane per unit weight of catalyst per hours (WWH) was 0.150.

EXAMPLE 6

The gaseous feed components were metered through mass flow controllers into the bottom of the reactor tube through the preheat leg. The catalyst was a catalyst of Example 1. Water was introduced through a septum at the top of the preheat leg using a syringe pump. The reaction temperature was 500° C., and the molar feed ratios were 1 propane / 2 $NH_3$ / 3 $O_2$ / 6.7 $N_2$ /3 $H_2O$. The collection of data began after 25 hours. Analysis of the reactor effluent showed that yield and selectivity of propane to acrylonitrile were 29.3 and 36.0 percent respectively; yield and selectivity to propylene were 4.4 and 5.5 percent, respectively.

EXAMPLE 7

The gaseous feed components were metered through mass flow controllers, into the bottom of the reactor tube through the preheat leg. The catalyst was a catalyst of Example 3. Water was introduced through a septum at the top of the preheat leg using a syringe pump. The reaction temperature was 500° C., and the molar feed ratios were 1 propane / 2 $NH_3$ / 3 $O_2$ / 6.7 $N_2$ / 3 $H_2O$. The collection of data began after 25 hours. Analysis of the reactor effluent showed that propane selectivity to acrylonitrile was 34.0 percent; and selectivity to propylene was 21.3 percent. The combined selectivity to acrylonitrile plus propylene was much greater than without P in the catalyst as in Example 6.

EXAMPLE 8

The gaseous feed components were metered through mass flow controllers into the bottom of the reactor tube through the preheat leg. The catalyst was a catalyst of Example 5. Water was introduced through a septum at the top of the preheat leg using a syringe pump. The reaction temperature was 500° C., and the molar feed ratios were 1 propane / 2 $NH_3$ / 3 $O_2$ / 6.7 $N_2$ / 3 $H_2O$. The collection of data began after 23 hours. Analysis of the reactor effluent showed that propane conversion was 72.3 percent, selectivity of propane to acrylonitrile was 38.4 percent and selectivity to propylene was 9.4 percent. The combined selectivity to desired products, acrylonitrile and propylene was 47.8 percent, compared to 41.5 percent in Example 6.

EXAMPLE 9

The gaseous feed components were metered through mass flow controllers into the bottom of the reactor tube through the preheat leg. The catalyst was the catalyst of Example 4. Water was introduced through a septum at the top of the preheat leg using a syringe pump. The reaction temperature was 500° C., and the molar feed ratios were 1 propane / 2 $NH_3$ / 3 $O_2$ / 6.7 $N_2$ / 3 $H_2O$. The collection of data began after 24 hours. Analysis of the reactor effluent showed that propane conversion was 78.2 percent; yield and selectivity of propane to acrylonitrile were 27.9 and 35.6 percent, respectively; yield and selectivity to propylene were 4.5 and 5.8 percent, respectively.

EXAMPLE 10

The gaseous feed components were metered through mass flow controllers into the bottom of the reactor tube through the preheat leg. The catalyst was a catalyst of Example 2. Water was introduced through a septum at the top of the preheat leg using a syringe pump. The reaction temperature was 500° C., and the molar feed ratios were 1 propane / 2 $NH_3$ / 3 $O_2$ / 6.7 $N_2$ / 3 $H_2O$. The collection of data began after 30 hours. Analysis of the reactor effluent showed that propane conversion was 86.2 percent; yield and selectivity of propane to acrylonitrile were 33.9 and 39.3 percent respectively; yield and selectivity to propylene were 4.2 and 5.9 percent, respectively. These results compared very favorably with Example 9, using the same catalyst except that it contained no P.

EXAMPLE 11

The gaseous feed components were metered through mass flow controllers into the bottom of the reactor tube through the preheat leg. The catalyst was a catalyst having the empirical composition $VSb_{3.5}P_{0.25}WO_x$, the same as Example 4 except for the P content. Water was introduced through a septum at the top of the preheat leg using a syringe pump. The reaction temperature was 500° C., and the molar feed ratios were 1 propane / 2 $NH_3$ / 3 $O_2$ / 6.7 $N_2$ / 3 $H_2O$. The collection of data began after 23 hours. Analysis of the reactor effluent showed that propane conversion was 87.3 percent; yield and selectivity of propane to acrylonitrile were 32.7 and 37.5 percent respectively; yield and selectivity to propylene were 3.4 and 3.9 percent, respectively.

In the ammoxidation runs of the following examples, the catalyst is in a tubular 3/8 in I.D. stainless steel fixed bed reactor. the reactor is equipped with a preheat leg immersed in a temperature controlling salt bath. These runs differed from previous runs in that an excess of propane was employed, so that conversions were necessarily low, but selectivities to useful products were high.

EXAMPLE 12

A catalyst having the composition 50 wt % $VSb_4PWO_x + 50$ wt % $Al_2O_3$ was made as follows: 2.99 g of ammonium vanadate and 6.98 g of ammonium metatungstate (85 wt % $WO_3$ equivalent) was dissolved in 100 ml of distilled water along with 2.95 g of 85% $H_3PO_4$ in 20 ml of distilled water. The mixture was heated to boiling. 14.92 g of $Sb_2O_3$ was then added along with a mixture consisting of 29.41 g of hydrated alumina, 85 wt % $Al_2O_3$ dispersed in about 104 ml of a 4% acetic acid solution. The mixture was heated to near boiling until it thickened. The thickened mixture was then placed on an evaporating dish and dried in an oven at 110° C. for about 16 hours. The dried material was heated in air at 350° C. for five hours and then ground and screened and the 20 to 35 mesh particle size was collected. the screened material was then heat treated in air at 610° C. for 3 hours.

0.28 g of the material was examined as a catalyst for propane ammoxidation in a fixed bed microreactor using a gaseous feed mixture consisting of $5C_3H_8$ / $1NH_3$ / $2O_2$ / $1H_2O$, a contact time of about 0.3 seconds, and a reaction temperature of 470° C. Analysis of the product mixture showed 13.4% propane had converted with selectivities to the useful products, acrylonitrile and propylene, of 16.1 and 60.7%, respectively.

EXAMPLE 13

A catalyst having the composition 50 wt % $VSb_3PWO_x + 50$ wt % $Al_2O_3$ was made as follows: 3.56 g of ammonium vanadate and 8.21 g of ammonium metatungstate (85 wt % $WO_3$ equivalent) were dissolved in 100 ml of distilled water along with 3.47 g of 85% $H_3PO_4$. 13.15 g of $Sb_2O_3$ was then added to the mxiture and the resulting slurry was heated for about one hour at about 90° C. A mixture consisting of 29.41 g of hydrated alumina, 85 wt % $Al_2O_3$ dispersed in 4.2 g of acetic acid in 100 ml of distilled water was then added to the slurry. After addition of the alumina, the mixture began to thicken. The thickened mixture was diluted with about 100 ml of water and the mixture was evaporated to near dryness on a hot plate with constant stirring. The material was then dried in an oven at 100° C. for about 16 hours. The dried material was heated in air at 350° C. for five hours and then ground and screened and the 20 to 35 mesh particle size was collected. The screened material was then heat treated in air at 610° C. for 3 hours.

The material was examined as a catalyst for propane ammoxidation using the same reaction conditions as Example 12. Propane conversion was 19.5% and selectivities to acrylonitrile and propylene were 20.9 and 53.0%, respectively.

EXAMPLE 14

A catalyst having the composition 50 wt % $VSbPWO_x + 50$ wt % $Al_2O_3$ was made as follows: 5.48 g of ammonium vanadate and 12.64 g of ammonium metatungstate (85 wt % $WO_3$ equivalent) were dissolved in 100 ml of distilled water along with 5.34 g of 85% $H_3PO_4$. 6.75 g of $Sb_2O_3$ was then added to the mixture and the resulting slurry was heated for about one hour at about 90° C. A mixture consisting of 29.41 g of hydrated alumina, 85 wt % $Al_2O_3$ dispersed in 4.2 g of acetic acid in 100 ml of distilled water was then added to the slurry. After addition of the alumina, the mixture began to thicken. The thickened mixture was diluted with about 100 ml of water and the mixture was evaporated to near dryness on a hot plate with constant stirring. The material was then dried in an oven at 100° C. for about 16 hours. The dried material was heated in air at 350° C. for five hours and then ground and screened and the 20 to 35 mesh particle size was collected. The screned material was then heat treated in air at 610° C. for 3 hours.

The material was examined as a catalyst for propane ammoxidation using the same reaction conditions as Example 12. Propane conversion was 20.7% and selectivities to acrylonitrile and propylene were 21.7 and 48.0%, respectively.

EXAMPLE 15

A catalyst having the composition 50 wt % $VSb_{3.5}P_{0.5}W_{0.5}O_x$+50 wt % $Al_2O_3$ was made as follows: 3.89 g of ammonium vanadate and 4.53 g of ammonium metatungstate (85 wt % $WO_3$ equivalent) were dissolved in 100 ml of distilled water along with 1.92 g of 85% $H_3PO_4$. 16.95 g of $Sb_2O_3$ was then added to the mixture and the resulting slurry was heated for about one hour at about 90° C. A mixture consisting of 29.41 g of hydrated alumina, 85 wt % $Al_2O_3$ dispersed in 4.2 g of acetic acid in 100 ml of distilled water was then added to the slurry. After addition of the alumina, the mixture began to thicken. The thickneed mixture was diluted with about 100 ml of water and the mixture was evaporated to near dryness on a hot plate with constant stirring. The material was then dried in an oven at 100° C. for about 16 hours. The dried material was heated in air at 350° C. for five hours and then ground and screened and the 20 to 35 mesh particle size was collected. The screened material was then heat treated in air at 610° C. for 3 hours.

The material was examined as a catalyst for propane ammoxidation using the same reaction conditions as Example 12. Propane conversion was 19.6% and selectives to acrylonitrile and propylene were 15.9 and 51.1%, respectively.

EXAMPLE 16

A catalyst having the composition 50 wt % $VSb_5P_{0.5}W_{0.5}O_x$+50 wt % $Al_2O_3$ was made as follows: 3.01 g of ammonium vanadate and 3.51 g of ammonium metatungstate (85 wt % $WO_3$ equivalent) were dissolved in 100 ml of distilled water along with 1.48 g of 85% $H_3PO_4$. 18.76 g of $Sb_2O_3$ was then added to the mixture and the resulting slurry was heated for about one hour at about 90° C. A mixture consisting of 29.41 g of hydrated alumina, 85 wt % $Al_2O_3$ dispersed in 4.2 g of acetic acid in 100 ml of distilled water was then added to the slurry. After addition of the alumina, the mixture began to thicken. The thickened mixture was diluted with about 100 ml of water and the mixture was evaporated to near dryness on a hot plate with constant stirring. The material was then dried in an oven at 100° C. for about 16 hours. The dried material was heated in air at 350° C. for five hours and then ground and screened and the 20 to 35 mesh particle size was collected. The screened material was then heat treated in air at 610° C. for 3 hours.

The material was examined as a catalyst for propane ammoxidation using the same reaction conditions as Example 12. Propane conversion was 13.3% and selectivities to acrylonitrile and propylene were 15.7 and 58.9%, respectively.

EXAMPLE 17

A catalyst having the composition 50 wt % $VSb_{3.5}P_{0.5}O_x$+50 wt % $Al_2O_3$ was made as follows: 4.59 g of ammonium vanadate were dissolved in 100 ml of distilled water along with 2.26 g of 85% $H_3PO_4$. 20.04 g of $Sb_2O_3$ was then added to the mixture and the resulting slurry was heated for about one hour at about 90° C. A mixture consisting of 29.41 g of hydrated alumina, 85 wt % $Al_2O_3$ dispersed in 4.2 g of acetic acid in 100 ml of distilled water was then added to the slurry. After addition of the Catapal, the mixture began to thicken. The thickened mixture was diluted with about 100ml of water and the mixture was evaporated to near dryness on a hot plate with constant stirring. The material was then dried in an oven at 100° C. for about 16 hours. The dried material was heated in air at 350° C. for five hours and then ground and screened and the 20 to 35 mesh particle size was collected. The screened material was then heat treated in air at 610° C. for 3 hours.

The material was examined as a catalyst for propane ammoxidation using the same reaction conditions as Example 12. Propane conversion was 15.9% and selectivities to acrylonitrile and propylene were 8.3 and 42.2%, respectively.

EXAMPLE 18

A catalyst having the composition 50 wt % $VSb_{3.5}P_{0.5}WO_x$+50 wt % $Al_2O_3$ was made as follows: 3.37 g of ammonium vandate and 7.85 g of ammonium metatungstate (85 wt % $WO_3$ equivalent) were dissolved in 100 ml of distilled water along with 1.66 g of 85% $H_3PO_4$. 14.69 g of $Sb_2O_3$ was then added to the mixture and the resulting slurry was heated for about one hour at about 90° C. A mixture consisting of 125 g of alumina sol (20 wt % $Al_2O_3$) was then added to the slurry. After addition of the sol, the mixture began to thicken. The thickened mixture was diluted with about 100 ml of water and the mixture was evaporated to near dryness on a hot plate with constant stirring. The material was then dried in an oven at 100° C. for about 16 hours. The dried material was heated in air at 350° C. for five hours and then ground and screened and the 20 to 35 mesh particle size was collected. The screened material was then heat treated in air at 610° C. for 3 hours.

The material was examined as a catalyst for propane ammoxidation using the same reaction conditions as Example 12. Propane conversion was 17.4% and selectivities to acrylonitrile and propylene were 18.5 and 53.5%, respectively.

EXAMPLE 19

A catalyst having the composition 50 wt % $VSb_{3.5}P_{0.5}WO_x$+50 wt % $Al_2O_3$ was made as follows: 3.40 g of ammonium vanadate and 7.85 g of ammonium metatungstate (85 wt % $WO_3$ equivalent) were dissolved in 100 ml of distilled water along with 1.66 g of 85% $H_3PO_4$. 14.69 g of $Sb_2O_3$ was then added to the mixture along with about 5 g of concentrated nitric acid solution. The resulting slurry was heated for about one hour at about 90° C. A mixture consisting of 29.41 g of hydrated alumina, 85 wt % $Al_2O_3$ dispersed in 4.2 g of acetic acid in 100 ml of distilled water was then added to the slurry. After addition of the alumina, the mixture began to thicken. The thickened mixture was diluted with about 100 ml of water and the mixture was evaporated to near dryness on a hot plate with constant stirring. The material was heated in air at 350° C. for five hours and then ground and screened and the 20 to 35 mesh particle size was collected. The screened material was then heat treated in air at 610° C. for 3 hours.

The material was examined as a catalyst for propane ammoxidation using the same reaction conditions as Example 12. Propane conversion was 19.5% and selectivities to acrylonitrile and propylene were 20.2 and 50.1%, respectively.

EXAMPLE 20

A catalyst having the composition 50 wt % $VSb_{3.5}P_{0.5}WO_x + 50$ wt % $Al_2O_3$ was made as follows: 3.20 g of ammonium vanadate and 7.38 g of ammonium metatungstate (85 wt % $WO_3$ equivalent) were dissolved in 100 ml of distilled water along with 1.56 g of 85% $H_3PO_4$. 127.59 g of antimony oxide sol was then added to the mixture along with 3.75 g of oxalic acid. The resulting slurry was heated for about one hour at about 90° C. A mixture consisting of 29.41 g of hydrated alumina, 85 wt % $Al_2O_3$ dispersed in 4.2 g of acetic acid in 100 ml of distilled water was then added to the slurry. After addition of the alumina, the mixture began to thicken. The thickened mixture was diluted with about 100 ml of water and the mixture was evaporated to near dryness on a hot plate with constant stirring. The material was then dried in an oven at 100° C. for about 16 hours. The dried material was heated in air at 350° C. for five hours and then ground and screened and the 20 to 35 mesh particle size was collected. The screened material was then heat treated in air at 610° C. for 3 hours.

The material was examined as a catalyst for propane ammoxidation using the same reaction conditions as Example 12. Propane conversion was 18.5% and selectivities to acrylonitrile and propylene were 15.8 and 48.6, respectively.

The following are additional catalyst compositions of the invention containing promoting amounts of phosphorus. When these are used under the conditions of Example 12 to ammoxidize propane, similarly high total selectivities to acrylonitrile plus propylene result.

50 wt % $VSb_5Sn_{0.5}Te_{0.5}Fe_{0.5}P_{0.5}WO_x + 50$ wt % $Al_2O_3$ 50 wt % $VSb_{3.5}P_{0.5}W_{0.5}Mo_{0.5}O_x + 50$ wt % $Al_2O_3$ 50 wt % $VSb_{3.5}P_{0.5}W_3O_x + 25$ wt % $Al_2O_3 + 25$ wt % $SiO_2$ 50 wt % $VSb_{10}CoNiP_{0.5}WO_x + 50$ wt % $Al_2O_3$ 50 wt % $VSb_5PWO_x + 40$ wt % $Al_2O_3 + 10$ wt % $MgO$ 50 wt % $VSb_3P_{0.5}WCs_{0.01}O_x + 50$ wt % $Al_2O_3$ 50 wt % $VSb_{10}P_3CrWO_x + 50$ wt % $Al_2O_3$ 50 wt % $VSbP_{0.5}B_3O_x + 40$ wt % $Al_2O_3 + 10$ wt % $Nb_2O_5$

As will be evident to those skilled in the art, various modifications of this invention can be made or followed in the light of the foregoing disclosure and discussion without departing from the spirit and scope of the disclosure or from the scope of the claims.

What is claimed is:

1. A complex metal oxide catalyst having ingredients and the proportions which are represented by the following empirical formula:

$$VSb_mP_nA_aD_bC_cT_tO_x$$

where
A is one or more of W, Sn, B and Ge;
D is one or more of Fe, Co, Ni, Cr, Mn, Cu, Zn, Se, Te, Pb and As;
C is one or more of an alkali metal and Tl;
T is one of more of Ca, Sr and BA;
and where m is 3–7; n is greater than zero and up to 10; a is 0.2–10; b is 0–3; c is 0–1; t is 0–1; a is equal to or less than m; b is equal to or less than m; n is equal to or less than m; and wherein the antimony has an average valency higher than +3, the vanadium has an average valency lower than +5, wherein A includes at least 0.2 atoms of W and the catalyst is essentially free of Mo and is on an inorganic support material selected from silica-alumina and alumina having 20 to 100 weight percent alumina.

2. A catalyst of claim 1 wherein n is 0.1 to 5.

3. A catalyst of claim 2 where a is at least 0.4.

4. A catalyst of claim 2 wherein A includes at least 0.4 atoms of W.

5. A complex metal oxide catalyst essentially free of Mo and having the ingredients and the proportions which are represented by the following empirical formula:

$$VSb_mP_nA_aD_bC_cT_tO_x$$

where A is one or more of W, Sn, B and Ge;
D is one or more of Fe, Co, Ni, Cr, Mn, Cu, Zn, Se, Te, Pb and As;
C is one or more of an alkali metal and Tl;
T is one or more of Ca, Sr and Ba;
and where m is more than 1 and up to 10; n is greater than zero and up to 10; a is 0.2–10; b is 0–3; c is 0–1; t is 0–1; a is equal to or less than m; b is equal to or less than m; n is equal to or less than m; and wherein the antimony has an average valency higher than +3, the vanadium has an average valency lower than +5, and wherein A includes at least 0.2 atoms of W.

6. A catalyst of claim 5 wherein n is 0.1 to 5.

7. A catalyst of claim 6 wherein A includes 0.4 atoms of W per atom of V.

8. A catalyst of claim 6 wherein m is 2–10.

9. A catalyst of claim 6 that includes an inorganic oxide support that does not includes an element of formula (1).

10. A catalyst of claim 9 wherein said support is selected from alumina, silica-alumina, silica, titania, silica-titania, Nb$_2$O$_5$, silica-niobia, silica-zirconia, zirconia and magnesia.

11. A catalyst of claim 9 wherein said support is selected from silica-alumina and alumina having 20 to 100 weight percent alumina; silica-titania and titania having 20–100 weight percent titania; silica-zirconia and zirconia having 80–100 weight percent zirconia; and silica-niobia and niobia having 30–100 weight percent niobia (Nb$_2$O$_5$).

12. A catalyst of claim 9 wherein said support contains 20–100 percent alumina and is selected from alumina and silica-alumina.

13. A catalyst of claim 9 wherein said support contains 50–100 percent alumina and is selected from alumina and silica-alumina.

14. A catalyst of claim 9 wherein said support contains 60–100 percent alumina and is selected from alumina and silica-alumina.

* * * * *